(12) United States Patent
Norcini et al.

(10) Patent No.: US 7,534,880 B2
(45) Date of Patent: May 19, 2009

(54) CLEAR PHOTOPOLYMERIZABLE SYSTEMS FOR THE PREPARATION OF HIGH THICKNESS COATINGS

(75) Inventors: Gabriele Norcini, Comabbio (IT); Stefano Romagnano, Gallarate (IT); Marco Visconti, Varese (IT); Giuseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 516 days.

(21) Appl. No.: 10/566,880

(22) PCT Filed: Aug. 3, 2004

(86) PCT No.: PCT/EP2004/051699

§ 371 (c)(1),
(2), (4) Date: Feb. 2, 2006

(87) PCT Pub. No.: WO2005/014515

PCT Pub. Date: Feb. 17, 2005

(65) Prior Publication Data

US 2006/0246228 A1 Nov. 2, 2006

(30) Foreign Application Priority Data

Aug. 7, 2003 (IT) .......................... VA2003A0028

(51) Int. Cl.
*C07D 265/30* (2006.01)
*C07C 49/213* (2006.01)

(52) U.S. Cl. .................... 544/175; 544/106; 544/170; 568/303; 568/308; 568/325

(58) Field of Classification Search ................ 544/106, 544/170, 175; 568/303, 308, 325
See application file for complete search history.

(56) References Cited

U.S. PATENT DOCUMENTS 3,715,293 A 2/1973 Sandner et al.
6,441,244 B1 * 8/2002 Avar et al. .................. 568/327
6,492,514 B1 12/2002 Meneguzzo et al.

FOREIGN PATENT DOCUMENTS

| DE | 27 22 264 | 5/1977 |
|---|---|---|
| EP | 0 003 002 | 7/1979 |
| EP | 0 088 050 | 2/1982 |
| EP | 0 161 463 | 11/1985 |
| EP | 0 192 967 | 9/1986 |
| EP | 0 284 561 | 3/1988 |
| EP | 0 850 253 | 3/1997 |

\* cited by examiner

*Primary Examiner*—Golam M Shameem
(74) *Attorney, Agent, or Firm*—Madan, Mossman & Sriram, P.C.

(57) ABSTRACT

The present invention relates to clear photopolymerisable systems for the preparation of high thickness coatings, to a procedure for their application and to the solid surfaces coated with them.

5 Claims, No Drawings

CLEAR PHOTOPOLYMERIZABLE SYSTEMS FOR THE PREPARATION OF HIGH THICKNESS COATINGS

TECHNICAL FIELD

This invention is related to clear photopolymerisable systems for the preparation of high thickness coatings, to a procedure for their application and to the solid surfaces coated with them.

In the present text, with the expression "high thickness coating" we mean a solid coating having thickness higher than 10 micron.

Particularly, the clear photopolymerisable systems of the invention include bifunctional photoinitlators of formula I:

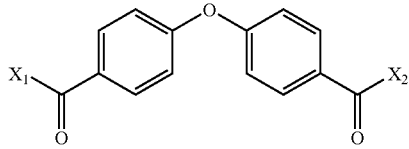
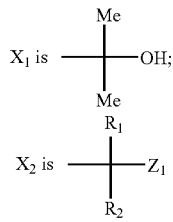

where $X_1$ and $X_2$ are different;

wherein $R_1$ and $R_2$ are independently linear or branched or cyclic $C_1$-$C_6$ alkyl, or together represent $C_2$-$C_6$ alkylene; $Z_1$ is —$NR_3R_4$ or —OH, and $R_3$ and $R_4$ are independently $C_1$-$C_6$ linear or branched or cyclic alkyl or $C_2$-$C_6$ oxaalkylene.

BACKGROUND ART

Known photopolymerisable systems contains photoinitiators characterised by the presence, within the molecule of a functional group that, by electromagnetic excitation, generally UV radiation, is able to generate radicals.

These compounds are described for example in U.S. Pat. No. 3,715,293, DE 2722264, EP 161463, EP 3002, EP 88050, EP 284561, EP 192967, EP 850253 and are usually used in the polymerisation of unsaturated ethylene systems.

In order to obtain a good polymerisation, both in surface curing and in through curing it is a common practice to associate within the formulation different photoinitiators.

In our previous patent U.S. Pat. No. 6,492,514 we described compounds containing within the same molecule two different active functional groups, both able to generate radicals by a photochemical process and showing high activity as photoinitiators.

These molecules can generate surprising synergies in comparison with the use of two photoinitiators each containing one of the two functional groups.

DISCLOSURE OF INVENTION

We have now found that, within the compounds of our previous patent U.S. Pat. No. 6,492,514, compounds of formula I

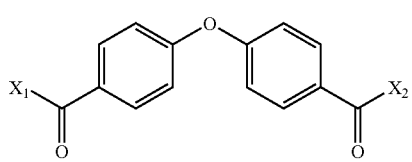

wherein $X_1$ and $X_2$ are different;

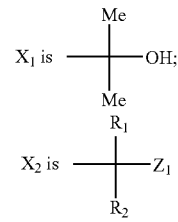

where $R_1$ and $R_2$ are independently linear or branched or cyclic $C_1$-$C_6$ alkyl, or together represent $C_2$-$C_6$ alkylene; $Z_1$ is —$NR_3R_4$ or —OH, and $R_3$ and $R_4$ are independently $C_1$-$C_6$ linear or branched or cyclic alkyl or $C_2$-$C_6$ oxaalkylene, in clear photopolymerisable systems useful for the realisation of through cure systems, surprisingly show a particularly high reactivity and an improved solubility within the formulations; clear photopolymerisable systems including these compounds show a better and faster crosslinking with respect to the analogous containing diphenilsulphide derivatives.

Clear systems including bifunctional compounds of formula I are particularly useful for the preparation of high thickness coatings, preferably having a thickness between 10 and 100 micron; they are a fundamental object of this invention.

In particular, the preferred clear photopolymerisable systems of the present invention include as photoinitiator at least one of the following compounds of formula Ia, Ib, Ic or Id:

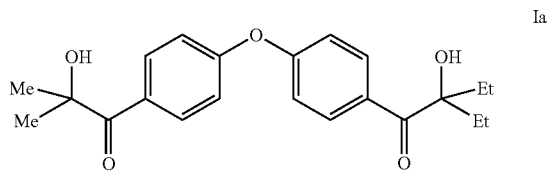

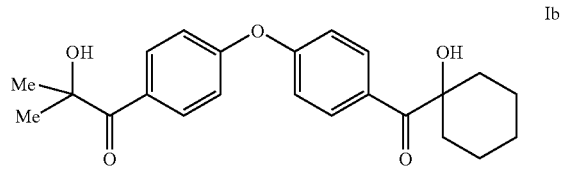

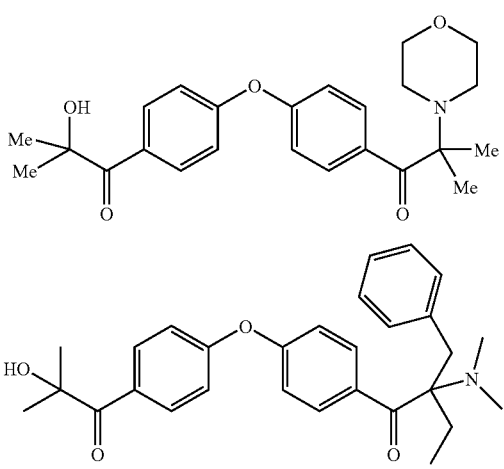

It is a further object of the present invention a procedure for the realisation of high thickness coatings for metal, wood or plastic surfaces, wherein the clear photopolymerisable system containing reactive ethylenically unsaturated oligomers and/or monomers and at least a bifunctional photoinitiator of formula I, preferably of formula Ia, Ib, Ic or Id is applied to obtain, after polymerisation, a coating having a thickness higher than 10 microns, preferably between 10 and 100 microns, and then photopolymerised with a light source emitting in the UV-visible spectrum up to 400 nm.

"Clear photopolymerisable system" and "clear photopolymerisable formulation" mean, in the present text, a mixture of reactive oligomers or monomers with at least a photoinitiator, fillers, dispersants and other additives of general use, devoid of pigments, dyes and/or opacifying agents, and dispersed solids.

The term "photopolymerisation" is intended in a wide sense and include, for example, the polymerisation or crosslinking of polymeric materials, such as for example pre-polymers, the homopolymerisation and the copolymerisation of simple monomers and the combination of this kind of reactions.

Monomers useful in the described system include for example: acrylonitrile, acrylamide and its derivatives, vinyl ethers, N-vinylpyrrolidone, mono and polyfunctional allyl ethers, such as for example trimethylolpropane diallylether, styrenes and alpha-methyl styrenes, esters of acrylic and methacrylic acid with alyphatic alcohols, with glycols, with polyhydroxylated compounds, as for example pentaerythrtol, trimethylolpropane or aminoalcohols, esters of vinyl alcohol with aliphatic or acrylic acids, derivatives of fumaric or maleic acids.

The oligomers which are useful for the present invention include, for example, polyesters, polyacrylates, polyurethanes, epoxydic resins, polyethers with acrylic, maleic or fumaric functionalities.

Compounds of formula I of the present invention acts as photoinitiators and can be used alone or in combination with other photoinitiators as for example benzophenone and its derivatives (such as methylbenzophenone, trimethylbenzophenone), acetophenone and its derivatives, for example α-hydroxyacetophenones, α-aminoacetophenones, ketosulphones (as 1-[4-(4-benzoyl-phenylsulfanyl)-phenyl]-2-methyl-2-(toluene-4-sulfonyl)-propan-1-one), α-hydroxycycloalkylphenyl ketones, dialcoxyacetophenone, (as oligo-[2-hydroxy-2-methyl-1-[4-(1-methylvinyl)phenyl]-propanone], 2-hydroxy-2-methyl-1-phenyl-propanone, 2-hydroxy-1-[4-(2-hydroxy-ethoxy)-phenyl]-2-methyl-propan-1-one, 2-dimethylamino-2-(4-methylbenzyl)-1-(4-morpholin-4-yl-phenyl)-butan-1-one, 2-benzyl-2-dimethylamino-1-(3,4-dimethoxy-phenyl)-butan-1-one, 2-benzyl-2-dimethylamino-1-(4-morpholin-4-yl-phenyl)-butan-1-one, 2-methyl-1-(4-methylsulfanyl-phenyl)-2-morpholin-4-yl-propan-1-one, 1-[2,3-dihydro-1-[4-(2-hydroxy-2-methyl-1-oxopropyl)phenyl]-1,3,3-trimethyl-1H-inden-5-yl]-2-hydroxy-2-methyl-1-propanone, 1-[2,3-dihydro-3-[4-(2-hydroxy-2-methyl-1-oxopropyl)phenyl]-1,1,3-trimethyl-1H-inden-5-il]-2-hydroxy-2-methyl-1-propanone, 4,3'-bis (α,α-hydroxy-isobutyryl)-diphenylmethane, 4,4'-bis(α,α-hydroxy-isobutyryl)-diphenylmethane, ethers of benzoin, benzyl ketales (as benzyl dimethyl ketal), phenylglyoxylates and its derivatives (as phenylglyoxylic acid methylester, ethyl ester of 2-(2-oxo-2-phenyl-acetoxy-etoxyethyl) oxyphenylacetic acid), monoacylphosphine oxides, as (2,4,6-trimethylbenzoyl)-diphenyl-phosphine oxide or the ethyl ester of phenyl-(2,4,6-trimethylbenzoyl)phosphinic acid, bisacylphosphine oxides, (as bis-(2,6-dimethoxybenzoyl)-(2,4,4-trimethyl-pent-1-yl)phosphine oxide, bis(2,4,6-trimethylbenzoyl)-phenyl-phosphine oxide, bis(2,4,6-trimethylbenzoyl)-(2,4-dipentoxyphenyl)phosphine oxide), trisacylphosphine oxides, halogenomethyltriazine, ferrocene or titanocene derivatives, photoinitiators containing the borate or O-acyloximic group, sulphonium, phosphonium or aromatic iodonium salts.

The use of the compounds of formula I in combination with tertiary amines, such as triethylamine, N-methyldiethanolamine, esters of p-dimethylamino benzoic acid, increasing the speed of crosslinking by reducing the inhibitory effect of the oxygen, has revealed to be particularly advantageous.

In addition to the compounds of formula I of the invention, many other components may be included in the photopolymerisable systems, for example thermal stabilisers, sensitisers, photooxydation stabilisers such as sterically hindered amines, antioxidants, oxygen inhibitors, thermal radicals generators such as organic and inorganic peroxides, peresters, hydroperoxides, benzopinacols, azoderivatives such as azaisobutyronitrile, metallic compounds such as cobalt(II) salts, manganese, antifoam, fillers, glass and carbon fibres, thixotropic agents and other additives.

Other components included in the photopolymerisable systems may be chemically inert non photopolymerisable polymers, as for example nitrocellulose, polyacrylic esters, polyolefines etc., or polymers which are crosslinkables with other systems, as for example with peroxides and atmospheric oxygen or acid catalysis or thermal activation, as for example polyisocyanates, urea, melamine or epoxydic resins.

It is important to note the utilisation of the photopolymerisable systems of the invention for the coating of solid substrates, as for example wood, paper, cardboard, plastic, metals, with a high thickness clear coating layer.

Solid substrates coated with a clear coating having a thickness between 10 and 100 microns obtained by photopolymerisation of a photopolymerisable system including at least one compound of formula Ia, Ib, Ic or Id are a further object of the invention.

The compounds of formula I are generally used in the photopolymerisable system in quantity of 0.01 to 20% in weight, preferably of 0.5 to 5% in weight, on the total weight of the photopolymerisable system and are perfectly compatible with the system, imparting to it an increased photochemical reactivity and light stability.

The compounds of formula I and particularly compounds Ia, Ib, Ic and Id show an excellent solubility in the common clear photopolymerisable systems.

The compounds of formula I are very efficient photoinitiators also in pigmented photopolymerisable systems and for example useful for the preparation of photocrosslinkable inks.

Examples of sources of light useful for the photopolymerisation of the photopolymerisable systems prepared according to the invention are mercury vapour or superactinic or excimers lamps, with emission bands in the UV-visible region until 400 nm.

Among the useful sources of light sunlight and other artificial sources emitting electromagnetic radiation with a wavelength from 180 nm up to the IR region are also included.

The compounds of formula I can be synthesised using different methods described in scientific literature and patents and well known by people skilled in the art.

Examples of the preparation of compounds of formula I and of clear and pigmented photopolymerisable systems containing them are herein reported.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims as set forth herein as follows.

EXAMPLE 1

Synthesis of 2-ethyl-2-hydroxy-1-{4-[4-(2-hydroxy-2-methyl-propionyl)-phenoxy]-phenyl}butan-1-one, Compound of Formula Ia 1. Preparation of 2-bromo-1-{4-[4-(2-bromo-2-methyl-propionyl)-phenoxy]-phenyl}-2-ethyl-butan-1-one 7.83 g (58.75 mmol) of $AlCl_3$ were added in portion to a solution of 10 g (58.75 mmol) of diphenylether and 15.4 g of 2-bromo-2-ethylbutyrylbromide (98.4% w/w) (58.75 mmol) in 100 ml of dichloromethane, under stirring, in 30', at a temperature between −10 and −12° C.

15' after the end of the addition, 15.24 g (64.62 mmol) of α-bromoisobutyrylbromide 97.5% were added; then, maintaining the temperature between −10 and −12° C., 8.61 g of $AlCl_3$ are added.

At the end of the addition the mixture was maintained under stirring for 1 h at the same temperature and then poured into 400 ml of water and ice and acidified with 8 ml of conc. HCl. The organic phase was separated, washed with brine, dried on sodium sulphate, and evaporated under vacuum.

29.15 g of product were obtained as an oil.

NMR (300 MHz, $CDCl_3$, δ (ppm)): 8.25, m, 2H; 8.15, m, 2H; 7.05, m, 4H; 2.3, m, 4H; 2.05, s, 6H; 0.95, t, 6H.

2. Preparation of 2-ethyl-2-hydroxy-1-{4-[4-(2-hydroxy-2-methyl-propionyl)-phenoxy]-phenyl}-butane-1-one To a solution of 29.15 g (0.0587 mol) of 2-bromo-1-{4-[4-(2-bromo-2-methyl-propionyl)-phenoxy]-phenyl}-2-ethyl-butane-1-one dissolved in 60 ml of dichloromethane, 16.88 g (0.211 mol) of 50% NaOH and 291.5 mg of 50% BTEAC were added. The reaction was refluxed for 3 h, adding every 30', 291.5 mg of BTEAC, then diluted with water and dichloromethane.

The phases were separated and the organic phase washed with brine, separated and dried on sodium sulphate, filtered and dried under vacuum.

20.2 g of compound were obtained as an oil.

NMR (300 MHz, $CDCl_3$, δ (ppm)): 8.13, d, 2H, 8.07, d, 2H, 7.1, m, 4H; 4.35, s, 1H; 3.97, s, 1H, 1.9-2.15, m, 4H, 1.65, s, 6H, 0.8, t, 6H.

EXAMPLE 2

Synthesis of 2-hydroxy-1-{4-[4-(1-hydroxy-cyclohexancarbonyl)-phenoxy]-phenyl}-2-methyl-propan-1-one, Compound of Formula Ib 1. Preparation of 2-bromo-1-[4-(4-cyclohexanecarbonyl-phenoxy)-phenyl]-2-methyl-propan-1-one 907 mg of $AlCl_3$ were added in one portion to a solution of 1.103 g (6.48 mmol) of diphenylether and 969 mg (6.48 mmol) of cyclohexylcarbonylchloride (98% w/w) in 10 ml of dichloromethane, at a temperature between 0 and 5° C. After 30' 1.68 g (7.13 mmol) of α-bromoisobutyrylbromide and 950 mg (7.13 mmol) of $AlCl_3$ were added between 0-5° C.

After 1 h, a second portion of 168 mg of α-bromoisobutyrylbromide and 95 mg of $AlCl_3$ were added. After 30' the reaction was poured into an aqueous solution containing 1% of concentrated HCl, the organic phase was separated, washed with brine and 5% $NaHCO_3$, dried on sodium sulphate, filtered and evaporated under vacuum.

2.8 g of product were obtained as yellow oil.

NMR (300 MHz, $CDCl_3$, δ (ppm)): 8.25, d, 2H, 7.97, d, 2H, 7.07, m, 4H; 3.25, m, 1H, 2.05, m, 6H; from 1.2 to 1.95, m, 10H 2. Preparation of 2-bromo-1-{4-[4-(1-bromo-cyclohexanecarbonyl)-phenoxy]-phenyl}-2-methyl-propan-1-one A drop of 48% HBr was added to a solution of 2.7 g (6.29 mmol) of 2-bromo-1-[4-(4-cyclohexancarbonyl-phenoxy)-phenyl]-2-methyl-propan-1-one dissolved in 60 ml of dichloromethane; 0.322 ml (6.29 mmol) of bromide dissolved in 5 ml of dichloromethane were added drop wise, in 15'. After 3 h, the organic phase was washed with water and with a sodium metabisulphite solution, separated, dried on sodium sulphate and evaporated in vacuum obtaining 3.2 g of product as a yellow oil.

NMR (300 MHz, $CDCl_3$, δ (ppm)): 8.25, d, 2H, 8.15, d, 2H, 7.1, m, 4H; 2.07, s, 6H; from 1.3 to 2.45, m, 10H 3. Preparation of 2-hydroxy-1-{4-[4-(1-hydroxy-cyclohexanecarbonyl)-phenoxy]-phenyl}-2-methyl-propan-1-one 1.83 g (22.86 mmol) of 50% NaOH and 32 mg of BTEAC were added to a solution of 3.2 g (6.29 mmol) of 2-bromo-1-{4-[4-(1-bromo-cyclohexanecarbonyl)-phenoxy]-phenyl}-2-methyl-propan-1-one in 10 ml of dichloromethane, The mixture was heated under stirring distilling off dichloromethane, until an internal temperature of 50° C. and then refluxed for 1 h, adding every 20' 32 mg of BTEAC. The solution was cooled, 10 ml of dichloromethane and 20 ml of water were added. After separation, the organic phase was washed with brine, dried over sodium sulphate, filtered and evaporated obtaining 2.3 g of an oily compound that crystallises on standing. The solid so obtained was triturated with petroleum ether and filtered.

2 g of a solid compound were obtained showing a solubility in TPGDA higher than 20%.

NMR (300 MHz, CDCl$_3$, δ (ppm)): 8.15, d, 2H, 8.07, d, 2H, 7.07, m, 4H, from 2.10 to 1.25, m, 10H, 1.65, s, 6H

EXAMPLE 3

Synthesis of 2-hydroxy-2-methyl-{4-[4-(2-methyl-2-morpholin-yl-propionyl)-phenoxy]-phenyl}-propan-1-one, Compound of Formula Ic

1. Preparation of 2-bromo-2-methyl-1-(4-phenoxy-phenyl)-propan-1-one 7.82 g of AlCl$_3$ were added in about 30' to a solution of 10 g (0.0587 mol) of diphenylether and 7.44 ml (0.0587 mol) of α-bromoisobutyrylbromide (97.5% w/w) in 100 ml of dichloromethane, maintaining the temperature between 0 e 5° C.

30' after the end of the addition the reaction was quenched in 200 ml of water and ice and 4 ml of concentrated HCl. The organic phase was separated, washed with water, dried on sodium sulphate and evaporated obtaining 18.7 g of an oil, used without further purification in the following reaction.

2. Preparation of 2-methoxy-3,3-dimethyl-2-(4-phenoxy-phenyl)-oxirane 17.6 g (0.0551 mol) of 2-bromo-2-methyl-1-(4-phenxy-phenyl)-propan-1-one were dissolved in 170 ml of methanol. 11 ml of a sodium methylate solution (30% in methanol) were added at room temperature. After 15' the solvent was evaporated and the product used without further purification in the following reaction.

3. Preparation of 2-methyl-2-morpholin-yl-1-(4-phenoxy-phenyl)-propan-1-one 14.89 g (0.0551 mol) of 2-methoxy-3,3-dimethyl-2-(4-phenoxy-phenyl)-oxirane were dissolved in 150 ml of anhydrous acetonitrile.

58.62 g of anhydrous lithium perchlorate (0.551 mol) and 48 g of morpholine (0.551 mol) were added under stirring. The reaction was refluxed for 4 hours and the solvent evaporated. The raw product was dissolved in water and extracted with dichloromethane and the organic phase washed 3 times with water, dried with sodium sulphate and evaporated. The raw product is then treated with 5% HCl and the aqueous phase extracted with diethyl ether (50 ml) then alkalinised with 10% NaOH and extracted with dichloromethane. The organic phase was washed with water, dried with sodium sulphate and evaporated.

12 g of a yellow oil are obtained and used without further purification in the following reaction.

NMR (300 MHz, CDCl$_3$, δ (ppm)): 8.6, d, 2H, 7.4, m, 2H, 7.24, m, 1H, 7.1, d, 2H, 6.95, d, 2H, 3.7, m, 4H, 2.6, m, 4H, 1.35, s, 6H.

4. Preparation of 1-{4-[4-(2-bromo-2-methyl-propionyl)-phenoxy]-phenyl}-2-methyl-2-morpholin-4-yl-propan-1-one 21.59 (0.162 mol) of AlCl$_3$ were added in portion to a solution of 12 g (0.0369 mol) of 2-methyl-2-morpholin-yl-1-(4-phenoxy-phenyl)-propan-1-one and 9.57 g of (0.0406 mol) of α-bromoisobutyrylbromide (97.5% w/w) in 240 ml of dichloromethane, between 0 and 5° C. under stirring. At the end of the addition the temperature was brought to 25° C. then after 2.5 h the reaction was quenched with 500 ml of water and ice. The organic phase was separated and washed with water and 5% NaOH, dried on sodium sulphate, filtered and evaporated obtaining 17.5 g of a reddish oil.

NMR (300 MHz, CDCl$_3$, δ (ppm)): 8.6, d, 2H, 8.25, d, 2H, 7.07, m, 4H, 3.7, m, 4H, 2.07, m, 4H, 2.05, s, 6H, 1.26, s, 6H

5. Preparation of 1-{4-[4-(2-hydroxy-2-methyl-propionyl)-phenoxy]-phenyl}-2-methyl-2-morpholin-4-yl-propan-1-one 5.31 g (0.0664 mol) of 50% NaOH and 175 mg of 50% BTEAC were added to a solution of 17.5 g (0.0369 mol) of 1-{4-[4-(2-bromo-2-methyl-propionyl)-phenoxy]-phenyl}2-methyl-2-morpholin-4-yl-propan-1-one in 35 ml of dichloromethane. The reaction was refluxed for 3 hours, adding 175 mg of BTEAC every hour, then diluted with 20 ml of dichloromethane and 20 ml of water. The organic phase was separated, washed with brine, and dried with sodium sulphate, filtered and evaporated in vacuum obtaining 14.7 g of an oil.

NMR (300 MHz, CDCl$_3$, δ (ppm)): 8.65, d, 2H, 8.13, d, 2H, 7.05, m, 4H; 4.03, s, 1H, 3.68, m, 4H, 2.57, m, 4H, 2.55, s, 6H, 1.35, s, 6H.

EXAMPLE 4 (COMPARATIVE)

Synthesis of 1-{4-[4-(2-hydroxy-2-methyl-propionyl)-phenylsulphanyl]-phenyl}-2-methyl-2-morpholin-4-yl-propan-1-one (Compound II)

1. Preparation of 2-bromo-2-methyl-1-(4-phenylsulphanyl-phenyl)-propan-1-one 7.01 g (0.0526 mol) of AlCl$_3$ are added in 30', between 0 e 5° C. to a solution of 10 g (0.0526 mol) of diphenilsulphide and 6.67 ml (0.0526 mol) of α-bromoisobutyrylbromide 97.5% (w/w) in 100 ml of dichloromethane. 30' after the end of the addition the reaction was poured into a mixture of 200 ml of water, ice and 4 ml of concentrated HCl. The organic phase was separated, washed with water, dried with sodium sulphate and evaporated obtaining 17.05 g of an oil, used without further purification in the following reaction NMR (300 MHz, CDCl$_3$, δ (ppm)): 8.1, d, 2H, 7.52, m, 2H, 7.4, m, 3H, 7.15, d, 2H, 2.05, s, 6H

2. Preparation of 2-methoxy-3,3-dimethyl-2-(4-phenylsulfanyl-phenyl)-oxirane 3 g (0.0551 mol) of 2-bromo-2-methyl-1-(4-phenylsulphanyl-phenyl)-propan-1-one were dissolved in 30 ml of methanol. 1.79 ml of a 30% sodium methylate solution in methanol at room temperature were added. After 15' the solution was evaporated and the product used without further purification in the following reaction.

3. Preparation of 2-methyl-2-morpholin-4-yl-1-(4-phenylsulphanyl-phenyl)-propan-1-one 2.56 g (8.94 mmol) of 2-methoxy-3,3-dimethyl-2-(4-phenylsulphanyl-phenl)-oxirane were dissolved in 30 ml of anhydrous acetonitrile then under stirring 9.51 g of anhydrous lithium perchlorate (89.4 mmol) and 7.79 g of morpholine (89.4 mmol) were added. The reaction was slightly refluxed for 4 hours, then the solvent was evaporated. The raw product was dissolved in water and extracted with dichloromethane. The organic phase was washed three times with water, dried with sodium sulphate and evaporated. The obtained product was purified by flash chromatography using dichloromethane as eluent obtaining 2.53 g of a yellowish oil.

NMR (300 MHz, δ (ppm)): 8.4, d, 2H, 7.53, m, 2H, 7.45, m, 1H, 7.15, d, 2H, 3.65, m, 4H, 2.55, m, 4H, 1.30, s, 6H

4. Preparation of 1-{4-[4-(2-bromo-2-methyl-propionyl)-phenylsulphanyl]-phenyl}-2-methyl-2-morpholin-4-yl-propan-1-one 4.30 (32.20 mol) of $AlCl_3$ were added in portion under stirring to a solution of 2.5 g (7.32 mmol) of 2-methyl-2-morpholin yl-1-(4-phenylsulphanyl-phenyl)-propan-1-one and 1.81 g (7.69 mmol) of α-bromoisobutyrylbromide (97.5% w/w) in 50 ml of dichloromethane, between 0 e 5° C. At the end of the addition the temperature was brought to 25° C. then, after 2.5 h, the reaction was quenched in 200 ml of iced water. The organic phase was separated and washed with water and 5% NaOH then dried with sodium sulphate, filtered and evaporated obtaining 3.59 g of product as a reddish oil.

NMR (300 MHz, $CDCl_3$, δ (ppm)): 8.55, d, 2H; 825, d, 2H, 7.4, m, 4H, 3.7, m, 4H, 2.51, m, 4H, 2.05, s, 6H, 1.35, s, 6H.

5. Preparation of 1-{4-[4-(2-hydroxy-2-methyil-propionyl)-phenylsulphanyl]-phenyl}-2-methyl-2-morpholin-4-yl-propan-1-one 1.05 g (13.18 mmol) of 50% NaOH and 35.9 mg of BTEAC (50%) were added to a solution of 3.59 g (7.32 mmol) of 1-{4-[4-(2-bromo-2-methyl-propionyl)-phenylsulfanyl]-phenyl}-2-methyl-2-morpholyn-4-yl-propan-1-one in 25 ml of dichloromethane. The reaction was refluxed for 3 hours, adding 35.9 mg of BTEAC every hour than diluted with 15 ml of dichloromethane and 15 ml of water. The organic phase was separated, washed with brine, dried with sodium sulphate, filtered and evaporated obtaining 2.93 g compound II as an oil.

NMR (300 MHz, $CDCl_3$, δ (ppm)): 8.65, d, 2H, 8.00, d, 2H, 7.4, m, 4H; 3.95, sb, 1H, 3.68, m, 4H, 2.57, m, 4H, 1.65, s, 6H, 1.30, s, 6H.

EXAMPLE 5 (COMPARATIVE)

Synthesis of 2-hydroxy-1-{4-[4-(1-hydroxy-cycloexancarbonyl)-phenylsulphanyl]-phenyl}-2-methyl-propan-1-one (compound III)

1. Preparation of 2-bromo-1-[4-(4-cyclohexancarbonyl-phenylsulphanyl)-phenyl]-2-methyl-propan-1-one 3.76 g of $AlCl_3$ in one portion were added to a solution of 5 g (26.84 mmol) of diphenylsulphide and 4.01 g (26.84 mmol) of cyclohexylcarbonylchloride (98% w/w) in 50 ml of dichloromethane, between 0 e 5° C. After 30', 6.96 g (29.52 mmol) of α-bromoisobutyrylbromide and 3.93 g (29.52 mmol) of $AlCl_3$ were added at 0-5° C.

After 1 h a second addition of 696 mg of α-bromoisobutyrylbromide and 393 mg of $AlCl_3$ was made. After 30', the reaction was poured into a solution of water and 1% conc. HCl, the organic phase was separated, washed with brine, dried with sodium sulphate, filtered and evaporated obtaining 11.95 g of a yellow oil.

NMR (300 MHz, $CDCl_3$, δ (ppm)): 8.15, d, 2H, 7.93, d, 2H, 7.47, d, 2H; 7.35, d, 2H, 3.23, m, 1H, 2.05, s, 6H; from 1.2 to 1.95, m, 10H

2. Preparation of 2-bromo-1-{4-[4-(1-bromo-cyclohexancarbonyl)-phenylsulphanyl]-phenyl}-2-methyl-propan-1-one A drop of 48% HBr was added to a solution of 11.95 g (26.83 mmol) of 2-bromo-1-[4-(4-cyclohexancarbonyl-phenylsulphanyl)-phenyl]-2-methyl-propan-1-one dissolved in 120 ml of dichloromethane; in 15' 1.37 ml (26.83 mmol) of bromine dissolved in 10 ml of dichloromethane were added drop wise. After 1 h the organic phase was washed with water and with a sodium metabisulphite solution. The organic phase was separated, washed with brine, dried with sodium sulphate, filtered and evaporated under vacuum obtaining 14.07 g of a yellowish oil.

NMR (300 MHz, $CDCl_3$, δ (ppm)): 8.12, d, 2H, 8.05, d, 2H, 7.4, m, 4H; 2.05, s, 6H; from 1.3 to 2.45, m, 10H

Preparation of 2-hydroxy-[(4-[4-(1-hydroxy-cyclohexanecarbonyl)-phenylsulphanyl]-phenyl]-2-methyl-propan-1-one 7.73 g (96.59 mmol) of 50% NaOH and 140.7 mg of BTEAC were added to a solution of 14.07 g (26.83 mmol) of 2-bromo-1-[4-(4-cyclohexanecarbonyl-phenylsulphanyl)-phenyl]-2-methyl-propan-1-one in 30 ml of dichloromethane.

The mixture was refluxed under stirring for 1 hour, adding every 30' 140.7 mg of BTEAC. The solution was cooled, then dichloromethane and water were added. After separation the organic phase was washed with brine, dried with sodium sulphate, filtered and evaporated under vacuum obtaining an oil that was triturated with petroleum ether, obtaining 9.2 g of product III, as a whitish solid showing a solubility of 8% ca. In TPGDA.

NMR (300 MHz, $CDCl_3$, δ (ppm)): 8.05, m, 4H, 7.40, m, 4H, 3.92,s, 1H; 3.15, s, 1H; from 2.10 to 0.9 m, 10H; 1.60, s, 6H

EXAMPLE 6

Synthesis of 2-benzyl-2-dimethylamino-1-{4-[4-(2-hydroxy-2-methyl-propionyl)-phenoxy]-phenyl}butan-1-one (Compound Id)

1. Preparation of 2-Bromo-2-methyl-1-(4-phenoxyphenyl)-propan-1-one 39.19 g of aluminium trichloride (0.294 mol) were added, between 0° C. and 5° C. In 45' to a solution of 50 g of diphenylether (0.294 mol) and 37.27 ml of α-bromoisobutyrylbromide in 250 ml of dichloromethane.

After 1 hour the reaction was quenched in a solution of 20 ml of conc. HCl in 400 ml of water at 0° C. The organic phase was separated, washed with brine, dried with sodium sulphate and evaporated obtaining 93.33 g of product as an yellowish oil.

NMR (300 MHz, $CDCl_3$, δ (ppm)): 8.2, d, 2H, 7.4, d, 2H, 7.2, m, 1H, 7.07, d, 2H, 6.95, d, 2H, 2.1, s, 6H Preparation of 2-hydroxy-2-methyl-1-(4-phenoxy-phenyl)-propan-1-one 69.4 g (0.347 mol) of 20% NaOH were added to a suspension of 92.33 g of 2-bromo-2-methyl-1-(4-phenoxy-phenyl)-propan-1-one in 100 ml of isopropanol. At the end of the reaction the product was completely dissolved. The reaction was neutralised with conc. HCl and isopropanol was evaporated. The residue was diluted with water and extracted with dichloromethane. The organic phase was separated, washed with water, dried with sodium sulphate and evaporated obtaining 71.84 g of product as a yellow oil.

NMR (300 MHz, CDCl$_3$, δ (ppm)): 8.04, d, 2H, 7.4, d, 2H, 7.2, m, 1H, 7.1, d, 2H, 7.00, d, 2H, 4.2, s, 1H; 1.6, s, 6H

3. Preparation of 2-bromo-1-{4-[4-(2-hydroxy-2-methyl-proplonyl)-phenoxy]-phenyl}-butan-1-one 7.8 g of aluminium trichloride (0.0585 mol) were added in portions between 0 and 5° C., in 10 minutes, to a solution of 5 g (0.0195 mol) of 2-hydroxy-2-methyl-1-(4-phenoxy-phenyl)-propan-1-one and 2.9 ml (0.0214 mol) of α-bromoisobutyrylbromide in 100 ml of dichloromethane. After one hour the reaction was quenched in a solution of 4 ml of concentrated HCl in 200 ml of water at 0° C. The organic phase was separated, washed with water, dried with sodium sulphate and evaporated obtaining 9 g of an yellow oil used without purification in the following reaction.

4. Preparation of 2-dimethylamino-1-{4-[4-(2-hydroxy-2-methyl-propionyl)-phenoxy]-phenyl}-butan-1-one A solution of 7.9 g (0.0195 mol) of 2-bromo-1-{4-[4-(2-hydroxy-2-methyl-propionyl)-phenoxy]-phenyl}-butan-1-one in diethyl ether was added drop wise to a solution of 58.5 ml of dimethylamine 2M in THF (0.117 mol), maintaining the temperature between 0° C. and 5° C. After one night the reaction was diluted with ether, washed three times with water, dried with sodium sulphate and evaporated obtaining 7.47 g of an oil used without purification in the following step.

5. Preparation of 2-benzyl-2-dimethylamino-1-{4-[4-(2-hydroxy-2-methyl-propionyl)-phenoxy]-phenyl}-butan-1-one To a solution of 7.2 g of 2-dimethylamino-1-{4-[4-(2-hydroxy-2-methyl-propionyl)-phenoxy]-phenyl}-butan-1-one in 70 ml of acetonitrile 2.78 ml (0.0234 mol) of benzyl bromide were added drop wise.

After 3 hours at room temperature the solvent was evaporated obtaining a semi-solid foam that was suspended in 70 ml of water and 70 ml of ethanol and 5.86 ml (0.0585 mol) of 30% NaOH were added and the reaction heated at 60° C. for 3 hours.

Ethanol was evaporated and the solution neutralised with acetic acid and extracted with diethyl ether.

The organic phase was separated, washed with water and dried with sodium sulphate obtaining 7 g of raw product that was purified by flash chromatography obtaining 4.7 g of product as a yellowish oil.

NMR (300 MHz, CDCl$_3$, d (ppm)): 8.4, d, 2H, 8.1, d, 2H, 7.0-7.3, m, 9H; 3.22, s, 2H, 2.4, s, 6H, 2.1, m, 1H, 1.85, m, 1H, 1.65,m, 6H, 0.70, t, 3H Application Tests.

Clear Photopolymerisable System.

The substances used for the preparation of the photopolymerisable systems evaluated in the following applicative tests are:

Ebecryl® 220 (hexafunctional aromatic urethane acrylate from UCB (Belgium);

OTA 480® (trifunctional oligomer acrylate derived from glycerol, from UCB, Belgium);

HDDA, (1,6-hexanedioldiacrylate; from UCB, Belgium).

As photoinitiators, the following compounds were used:
2-ethyl-2-hydroxy-1-{4-[4-(2-hydroxy-2-methyl-propionyl)-phenoxy]-phenyl}-butan-1-one (Ia);
2-hydroxy-1-{4-[4-(1-hydroxy-cyclohexanecarbonyl)-phenoxy]-phenyl}-2-methyl-propan-1-one (Ib);
2-hydroxy-2-methyl-1-{4-[4-(2-methyl-2-morpholin-4-yl-propionyl)-phenoxy]-phenyl}-propan-1-one (Ic);
2-benzyl-2-dimethylamino-1-{4-[4-(2-hydroxy-2-methyl-propionyl)-phenoxy]-phenyl}-butan-1-one (Id);
1-{4-[4-(2-hydroxy-2-methyl-propionyl)-phenylsulphanyl]-phenyl}-2-methyl-2-morpholin-4-yl-propan-1-one (II, comparative);
2-hydroxy-1-{4-[4-(1-hydroxy-cyclohexanecarbonyl)-phenylsulphanyl]-phenyl}-2-methyl-propan-1-one (III, comparative)

A matrix for the photopolymerisable systems to be evaluated was prepared mixing (% w/w):

| | |
|---|---|
| Ebecryl 220 ® | 75% |
| OTA 480 ® | 12.5% |
| HDDA | 12.5% |

The photopolymerisable systems are prepared; their compositions are reported in Table 1 (% w/w).

TABLE 1

| | A | B | B' | C | C' | D | S* | S'* | SS* | SS'* |
|---|---|---|---|---|---|---|---|---|---|---|
| Matrix | 96 | 96 | 98 | 96 | 98 | 96 | 96 | 98 | 96 | 98 |
| Comp. Ia | 4 | | | | | | | | | |
| Comp. Ib | | 4 | 2 | | | | | | | |
| Comp. Ic | | | | 4 | 2 | | | | | |
| Comp. Id | | | | | | 4 | | | | |
| Comp. II | | | | | | | 4 | 2 | | |
| Comp. III | | | | | | | | | 4 | 2 |

*comparative

The evaluation of the photocrosslinkable systems was done by determining the reactivity, through cure, percentage of conversion and yellow and white indexes.

Reactivity.

The photopolymerisable system is laid with a thickness of 50 microns on a varnished cardboard using a bar-coater mounted on an electric stretch-film and therefore irradiated at a distance of 26 cm from the light source. A Giardina® photopolymerisator was used, equipped with a medium pressure mercury lamp with a power of 80 W/cm.

The thickness of the coating after photocrosslinking is 37 micron (measured with a Minitest 3000 apparatus).

The photopolymerisation speed, measured in m/min, is the maximum possible speed that results in a perfect superficial crosslinking of the system ("tack free"); the superficial crosslinking is assumed to be perfect when the surface is not damaged with the "thumb twist test".

The maximum speed (expressed in m/min) that results in a surface resisting to any visible damage after rubbing with abrasive paper was also measured (superficial abrasion).

The greater is the maximum speed, the greater is the efficiency of the system.

The obtained results are reported in Table 2.

TABLE 2

|  | A | B | C | D | S* | SS* |
|---|---|---|---|---|---|---|
| Tack-free (m/min) | 23.5 | 32.3 | 35.5 | 30.0 | 18.5 | 13.0 |
| Superficial abrasion (m/min) | 18.5 | 24.2 | 22.0 | 15.0 | 12.5 | 11.3 |

*comparative

Through-cure.

The photopolymerisable system is laid with a thickness of 100 micron, with a bar-coater mounted on an electric stretch-film, on a glass support then irradiated at a distance of 26 cm from the light source at a speed of 10 m/min. A Giardina® photopolymerisator was used, equipped with a medium pressure mercury lamp with a power of 80 W/cm.

The thickness of the photopolymerisable system after crosslinking is 65 micron (measured with a Minitest 3000 apparatus)

Through-cure was determined by ISO 1522-1998 standard test method, measuring the pendulum hardness, an index of the elasticity of the photocrosslinked system.

The higher the hardness (long time of pendulum oscillations), the lower the elasticity of the coating and the higher the total crosslinking, also in depth, of the coating.

The obtained results are reported in Table 3.

TABLE 3

|  | C | D | S* |
|---|---|---|---|
| Hardness (in seconds of oscillation) | 160 | 140 | 139 |

*comparative

White and Yellow Index

The photopolymerisable system is laid with a thickness of 100 microns on a varnished cardboard using a bar-coater mounted on an electric stretch-film and then is passed at a distance of 26 cm from the light source and a speed of 10 m/min. A Giardina® photopolymerisator was used, equipped with a medium pressure mercury lamp with a power of 80 W/cm.

White and yellow indexes were measured according to ASTM D1925-70 standard test method. A low value of yellow index and a high value of white index, correspond to a good stability of the colour of the formulation.

The results are reported in Table 4.

TABLE 4

|  | A | B | C | D | S* |
|---|---|---|---|---|---|
| Yellow Index | 12.6 | 12.5 | 13.9 | 17.4 | 18.0 |
| White Index | 50.4 | 50.6 | 47.1 | 42.4 | 37.3 |

*comparative

Application test.
Pigmented system.
Reactivity

The photopolymerisable system is laid with a thickness of 3 microns on a varnished cardboard using a bar-coater mounted on an electric stretch-film and therefore irradiated at a distance of 26 cm from the light source. A Fusion® photopolymerisator was used, equipped with a medium pressure mercury lamp with a power of 120 W/cm.

The photopolymerisation speed, measured in m/min, is the maximum possible speed that results in a perfect superficial crosslinking of the system ("tack free"); the superficial crosslinking is assumed to be perfect when the surface is not damaged with the "thumb twist test".

The matrix for the pigmented photopolymerisable systems to be evaluated was a blue acrylic ink from Piacentini S.p.A.

As photoinitiators, the following compounds were used:

2-ethyl-2-hydroxy-1-{4-[4-(2-hydroxy-2-methyl-proplonyl)-phenoxy]-phenyl}-butan-1-one (Ia);

2-hydroxy-1-{4-[4-(1-hydroxy-cycloexanecarbonyl)-phenoxy]-phenyl}-2-methyl-propan-1-one (Ib);

2-hydroxy-2-methyl-1-(4-[4-(2-methyl-2-morpholin-4-yl-propionyl)-phenoxy]-phenyl)-propan-1-one (Ic);

-2-benzyl-2-dimethylamino-1-{4-[4-(2-hydroxy-2-methyl-propionyl)-phenoxy]-phenyl}butan-1-one (Id);

isobutylthioxantone (ITX)

The compounds were evaluated alone (3% w/w) in the formulation and sensitsed with 0.5% of ITX.

The results are reported in Table 5

TABLE 5

|  | Tack Free (m/min) | Tack free (m/min) with ITX 0.5% |
|---|---|---|
| Ia | 21 | 26 |
| Ib | 20 | 26 |
| Ic | 18 | 28 |
| Id | 20 | 34 |

Percentage of Conversion

The photopolymerisable system is laid with a thickness of 12 micron using a bar-coater mounted on an electric stretch-film on a polyethylene sheet.

An IR spectra was registered in absorbance and the peak area at 1405 cm$^{-1}$ was measured, keeping as reference the area of the peak at 1725 cm$^{-1}$ ($A_o$).

The photopolymerisable system is then irradiated with a Fusion photopolymerisator equipped with a medium pressure mercury lamp with a power of 120 W/cm at a speed of 50 m/min.

The IR spectrum is then registered in absorbance and the peak area at 1405 cm$^{-1}$ is measured again, keeping the same reference (A); the peak area at 1725 cm$^{-1}$ is not affected by the photopolymerisation.

The value of the conversion percentage (% C) was calculated with the following formula:

% $C = 100 - [(A/A_0) \times 100]$ and is an index of the crosslinking degree of the system (both on the surface and in depth).

The results are reported in Table 6 and 7.

TABLE 6

|  | C' | S'* |
|---|---|---|
| % conversion | 58 | 53 |

*comparative

TABLE 7

|  | B' | SS'* |
|---|---|---|
| % conversion | 59 | 51 |

*comparative

As it is shown from the reported data, the presence of photoinitiators of formula I is responsible for a high reactivity of the tested photopolymerisable systems, of complete crosslinking in depth and good yellow and white indexes.

The invention claimed is:
1. A photoinitiator of formula Ic:

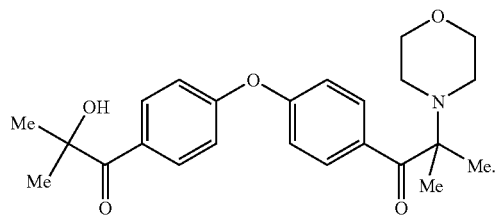

Ic

2. A photoinitiator of formula Id:

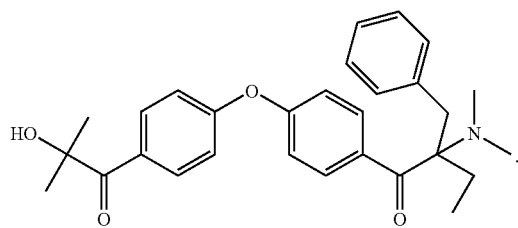

Id

3. A photopolymerizable system comprising one or more bifunctional photoinitiators having the formula I:

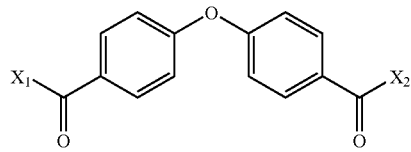

I wherein $X_1$ and $X_2$ are different;

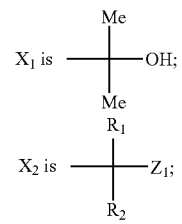

and wherein
$R_1$ and $R_2$ are independently linear or branched or cyclic $C_1$-$C_6$ alkyl, or together represent $C_2$-$C_6$ alkylene;
$Z_1$ is —$NR_3R_4$; and
$R_3$ and $R_4$ are independently C1-C6 linear or branched or cyclic alkyl $C_2$-$C_6$ oxaalkylene.

4. The photopolymerizable system of claim 3 wherein at least one photoinitiator has the formula Ic:

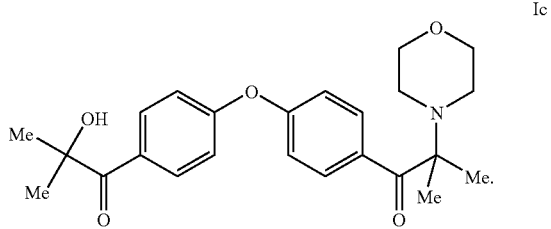

Ic

5. The photopolymerizable system of claim 3 wherein at least one photoinitiator has the formula Id:

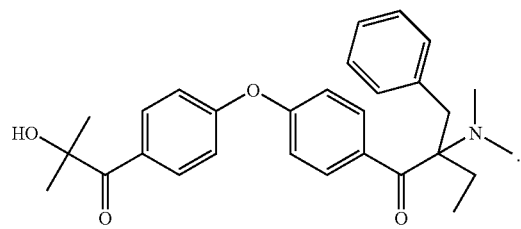

Id

* * * * *